United States Patent
Cha et al.

(10) Patent No.: US 6,778,927 B2
(45) Date of Patent: Aug. 17, 2004

(54) SYSTEM AND METHOD OF OBTAINING MEASURING CHARACTERISTIC CORRECTION FACTORS FOR RESPIRATORY FLOW MEASURING DEVICE USING STATIC PRESSURE DIFFERENCE

(76) Inventors: Un Jong Cha, 208-205, Jugong 2 Apt., Mochung-dong, Heungdeok-gu, CheongJu-city, Cungcheongbuk-Do (KR); Hyun Sik Kim, 604-1101, Kukhwa-hansin Apt, Samcheon-dong, Seo-gu, Daejeon metropolitan city (KR); Kyoung A Kim, 1207, Deokhee Apt., Sajik 2-dong, Heungdeok-gu, CheongJu-city, Cungcheongbuk-Do (KR)

( * ) Notice: Subject to any disclaimer, the term of this patent is extended or adjusted under 35 U.S.C. 154(b) by 0 days.

(21) Appl. No.: 10/325,877
(22) Filed: Dec. 23, 2002
(65) Prior Publication Data
US 2003/0171887 A1 Sep. 11, 2003
(30) Foreign Application Priority Data
Jan. 9, 2002 (KR) ................................. 10-2002-0001151
(51) Int. Cl.[7] ............................. G06F 15/00; G06F 1/12
(52) U.S. Cl. ........................ 702/100; 600/638; 600/639; 703/861.42; 702/45

(58) Field of Search .............................. 73/861, 861.42, 73/861.52; 700/282–285; 702/100, 138, 139, 45, 47; 600/537, 538

(56) References Cited

U.S. PATENT DOCUMENTS

| | | | | |
|---|---|---|---|---|
| 5,816,246 A | * | 10/1998 | Mirza | 600/539 |
| 6,090,049 A | * | 7/2000 | Cha | 600/538 |
| 6,585,662 B1 | * | 7/2003 | Jones et al. | 600/538 |

* cited by examiner

Primary Examiner—Kamini Shah
(74) Attorney, Agent, or Firm—Birch, Stewart, Kolasch & Birch, LLP

(57) ABSTRACT

The present invention relates to a system (1) for obtaining measuring characteristic correction factors for a respiratory flow measuring device (50) using a differential pressure difference. The system (1) has a 3 L syringe (10), a detecting unit (20), an A/D converter (30) and a computer (40). The 3 L syringe (10) is connected to a respiratory tube of the respiratory flow measuring device (50) through a duct line. The detecting unit (20) detects volume variation within the syringe (10) and outputs the detected result as a voltage signal. The A/D converter (30) converts a volume variation signal, detected as the voltage signal by the detecting unit (20), and a differential pressure variation signal, detected as a voltage signal by a differential pressure sensor (54) through a signal extracting circuit (56) into digital signals. The computer (40) calculates measuring characteristic correction factors using the digital signals.

3 Claims, 8 Drawing Sheets

SYSTEM AND METHOD OF OBTAINING MEASURING CHARACTERISTIC CORRECTION FACTORS FOR RESPIRATORY FLOW MEASURING DEVICE USING STATIC PRESSURE DIFFERENCE

BACKGROUND OF THE INVENTION

1. Field of the Invention

The present invention relates generally to a system and method of obtaining measuring characteristic correction factors for a respiratory flow measuring device using a static pressure difference, and more particularly to a system and method of obtaining measuring characteristic correction factors for a pneumotachometer most generally used for respiratory flow measurement.

2. Description of the Prior Art

As well known to those skilled in the art, a pneumotachometer is widely used to examine the capacity of the lungs. The pneumotachometer is constructed to measure the difference between static pressures generated via a fluid resistor in the center of a cylindrical tube using a differential pressure sensor connected to the cylindrical tube. In such a pneumotachometer, when respiratory airflow passes through a fluid resistor, energy is lost due to friction with the fluid resistor, thus generating a differential pressure due to the loss of energy. Accordingly, this device is constructed to calculate respiratory flow by measuring the differential pressure. The pneumotachometer is designed to change the sign of the differential pressure when the direction of the respiratory airflow is reversed, thereby continuously measuring the respiratory flow of a human body, flowing in both directions of exhalation and inhalation. When respiratory flow is measured by the pneumotachometer, the relationship between differential pressure $\Delta P$ and respiratory flow F is regulated by an experimentally-derived characteristic equation. Typically, since a fluid resistor R is represented by a linear function of a flow, the differential pressure $\Delta P$ is expressed by a quadratic function of the respiratory flow F as indicated in Equation [1] which is Rohrer's equation.

$$\Delta P = R(F) \cdot F \quad [1]$$
$$= (R_0 + R_1 F) \cdot F$$
$$= R_0 F + R_1 F^2$$

In Equation [1], if coefficients $R_0$ and $R_1$, representing measuring characteristics, are already known, the respiratory flow F can be determined by measuring $\Delta P$ using the following Equation [2].

$$F = \frac{\sqrt{R_0^2 + 4R_1 \cdot \Delta P} - R_0}{2R_1} \quad [2]$$

In Equation [2], $R_0$ and $R_1$ are individually determined with respect to both directional respiratory airflows of the human body (inhalation and exhalation).

Meanwhile, since there are two measuring characteristic coefficients $R_0$ and $R_1$ in Equation [1], $\Delta P$ and F are not proportional to each other, so the measuring characteristic coefficients can be determined only when a pair of $\Delta P$ and F are measured at two or more points.

A rotometer is generally used as a device for determining the characteristic coefficients, which is operated as follows.

First, when respiratory airflow with a certain flow rate is allowed to flow into a respiratory tube of a pneumotachometer by operating a vacuum pump, attractive force is generated by the vacuum pump within a glass tube which is arranged perpendicularly to the respiratory tube to communicate with the vacuum pump. The attractive force lifts a pendulum in the glass tube. At this time, airflow is generated between the pendulum and the wall of the glass tube, so the flow of the airflow moving in the tube is constant.

In this case, the pendulum ascends to a height at which the weight of the pendulum becomes equal to the attractive force, and the attractive force is proportional to the flow generated by the vacuum pump, so the height of the pendulum is proportional to the flow, that is, H∝F. Further, the airflow with the same flow as that of the respiratory tube goes into the pneumotachometer to generate a differential pressure $\Delta P$.

Thereafter, if multivariate regression analysis adopting Equation [1] as a model equation is performed after several data pairs of $\Delta P$ and F are measured by varying the attractive force of the vacuum pump to desired intensities, the measuring characteristic coefficients $R_0$ and $R_1$ which best satisfy the measured pairs of $\Delta P$ and F can be obtained. Since the $R_0$ and $R_1$ are determined, the measuring characteristic coefficients $R_0$ and $R_1$ are applied to Equation [2], thus measuring new airflow, that is, respiratory flow. In this case, the determined measuring characteristics are characteristics under steady flow, that is, static characteristics.

However, since the measuring characteristics are static characteristics, they are obtained under the measuring environments differing greatly from dynamic airflow in which flow is instantaneously changed, like the respiratory airflow of the human body.

In order to compensate for the static characteristics, the American Thoracic Society (ATS) recommends that a 3 L syringe similar to the volume of the lungs of the human body is connected to a pneumotachometer, and the respiratory flow of the human body is simulated by manually reciprocating the handle of the syringe (refer to Am. J. Respir. Crit. Care Med. Vol. 152: 1107–1136, 1995).

All of airflows generated by the syringe flow into the pneumotachometer, and the volume of the syringe is uniformly 3 L. Therefore, if the flow signal measured by the pneumotachometer is integrated, the integrated result must be 3 L. However, since the measuring characteristic coefficients Ro and R1 which are previously calculated may not be ideal, the following Equation [3] is obtained if a proportional coefficient S is introduced and formulated.

$$S = \frac{V_C}{\int F(t)dt} = \frac{3}{\int F(t)dt} \quad [3]$$

In Equation [3], $V_C$ is the volume of the syringe, and the proportional coefficient S corrects the integrated value of the airflow to be $V_C$=3 L by scaling the measured airflow at a predetermined rate regardless of the instantaneous value of the airflow.

The user of a respiratory airflow sensor measures respiratory airflow by using a mean value $\bar{s}$ of the values of the proportional coefficient S obtained by repeatedly performing manual reciprocation of the syringe as an ultimate correction coefficient.

This method is widely used because of the convenience of the user's ability to calibrate the pneumotachometer without an additional device except for the syringe. Generally, this method is carried out such that the user derives the following Equation [4], which is an ultimate characteristic equation, by further obtaining the mean value $\bar{s}$ of the values of the proportional coefficient S, besides the measuring characteristic coefficients $R_0$ and $R_1$ determined by a manufacturing company, and then measures respiratory flow.

$$F = \bar{s} \cdot \frac{\sqrt{R_0^2 + 4R_1 \cdot \Delta P} - R_0}{2R_1} \quad [4]$$

However, since Equation [1] is an experimentally-derived characteristic equation, Equation [4], which is derived from Equation [1], cannot provide the same accuracy for flow values of all airflows. Referring to fluid resistor-flow characteristics shown in FIG. 8, it can be seen that random errors are always present along linear flow values.

Therefore, errors incapable of being expressed by equations according to flow values are generated, and they overlap each other in the case of commercialized respiratory flow measuring devices, such that volume measurement error reaches 8% maximally (Journal of the Korean Society of Medical Informatics Vol. 6, pp 67–78, 2000).

Further, in a method of calibrating the respiratory flow measuring device by calculating the proportional coefficient S using the syringe after obtaining $R_0$ and $R_1$ through the static characteristic measuring experiment, $R_0$ and $R_1$ are not accurate with respect to flow values of all of airflows as described above, so the proportional coefficient S obtained by the Equation [3] is not constant. Further, since the same coefficients determined under the static environments are actually used under dynamic environments, the distortion of the values of the proportional coefficient S would be further increased.

In fact, as the result of a syringe experiment carried out by using the same coefficients obtained in static characteristic experiments of a pneumotachometer disclosed in U.S. Pat. No. 6,090,049, error which is not negligible is observed (relative error of maximum 7.5%), as shown in FIG. 9. Even though this error is corrected by Equations [3] and [4], the values of the proportional coefficient S are not constant and vary according to the characteristics of airflows.

Further, the conventional method of correcting measuring characteristics for respiratory flow is problematic in that, since measuring characteristics are inevitably uniformly corrected using a single proportional coefficient S without regard to the relative ratio of the characteristic coefficients $R_0$ and $R_1$, the user cannot correct measuring characteristics if the proportional relationship between $R_0$ and $R_1$ is varied due to the measuring environment, or if there is original error when $R_0$ and $R_1$ were determined.

Consequently, the measuring characteristic correction method and device is problematic in that, since it includes the cause of the inevitable measurement error, and requires a device for generating certain flow and a rotometer, measuring characteristic correction is excessively complicated and high cost is required, thus greatly decreasing accuracy and economic efficiency.

SUMMARY OF THE INVENTION

Accordingly, the present invention has been made keeping in mind the above problems occurring in the prior art, and an object of the present invention is to provide a system, which can conveniently and inexpensively obtain measuring characteristic correction factors, enabling a respiratory flow measuring device to more accurately measure respiratory flow compared with a conventional respiratory flow measuring device when respiratory flow is measured using the respiratory flow measuring device that utilizes static pressures, such as a pneumotachometer.

Another object of the present invention is to provide a method of obtaining measuring characteristic correction factors used in respiratory flow measurement while eliminating measurement error due to differences between characteristic equation calculating environments (static characteristics) and correcting environments (dynamic airflow), which is inevitably generated in a conventional respiratory flow measuring characteristic correction method.

In order to accomplish the above objects, the present invention provides a system for obtaining measuring characteristic correction factors for a respiratory flow measuring device using a static pressure difference, comprising a syringe connected to a respiratory tube of the respiratory flow measuring device through a duct line; a detecting unit for detecting volume variation within the syringe and outputting the detected result as a voltage signal; an analog/digital (A/D) converter for converting analog signals including a volume variation signal detected as the voltage signal by the detecting unit and a differential pressure variation signal detected as a voltage signal by a differential pressure sensor connected to the respiratory flow sensor of the respiratory flow measuring device into digital signals; and a computer for collecting the digital signals outputted from the A/D converter to calculate measuring characteristic correction factors.

Further, the present invention provides a method of obtaining measuring characteristic correction factors required for respiratory flow measurement using a measuring characteristic correction factor obtaining system, comprising the step of calculating characteristic coefficients $R_0$ and $R_1$ of the above Equation [1] by applying an instantaneous flow value F(t) obtained by differentiating the volume variation signal V(t), converted by the A/D converter, and the differential pressure variation signal $\Delta P(t)$, converted by the A/D converter, to the following Equation [8].

Further, the measuring characteristic correction factor obtaining method of the present invention comprises the steps of drawing up a histogram according to strokes using differential pressure variation signal information accumulated in a manual reciprocation experiment of the syringe to calculate a volume measurement value after calculating the measuring characteristic coefficients $R_0$ and $R_1$, obtaining the ratio $S_k$ of an actual volume value to the volume measurement value, and calculating a correction coefficient gi for correcting the volume measurement value according to respiratory flow values by applying the ratio $S_k$ to the following Equation [23].

BRIEF DESCRIPTION OF THE DRAWINGS

The above and other objects, features and other advantages of the present invention will be more clearly understood from the following detailed description taken in conjunction with the accompanying drawings, in which:

FIG. 3b is a graph showing the frequency of the flow sampling value of FIG. 3a;

DESCRIPTION OF THE PREFERRED EMBODIMENTS

Hereinafter, embodiments of the present invention will be described in detail with reference to the attached drawings.

Figure 1:
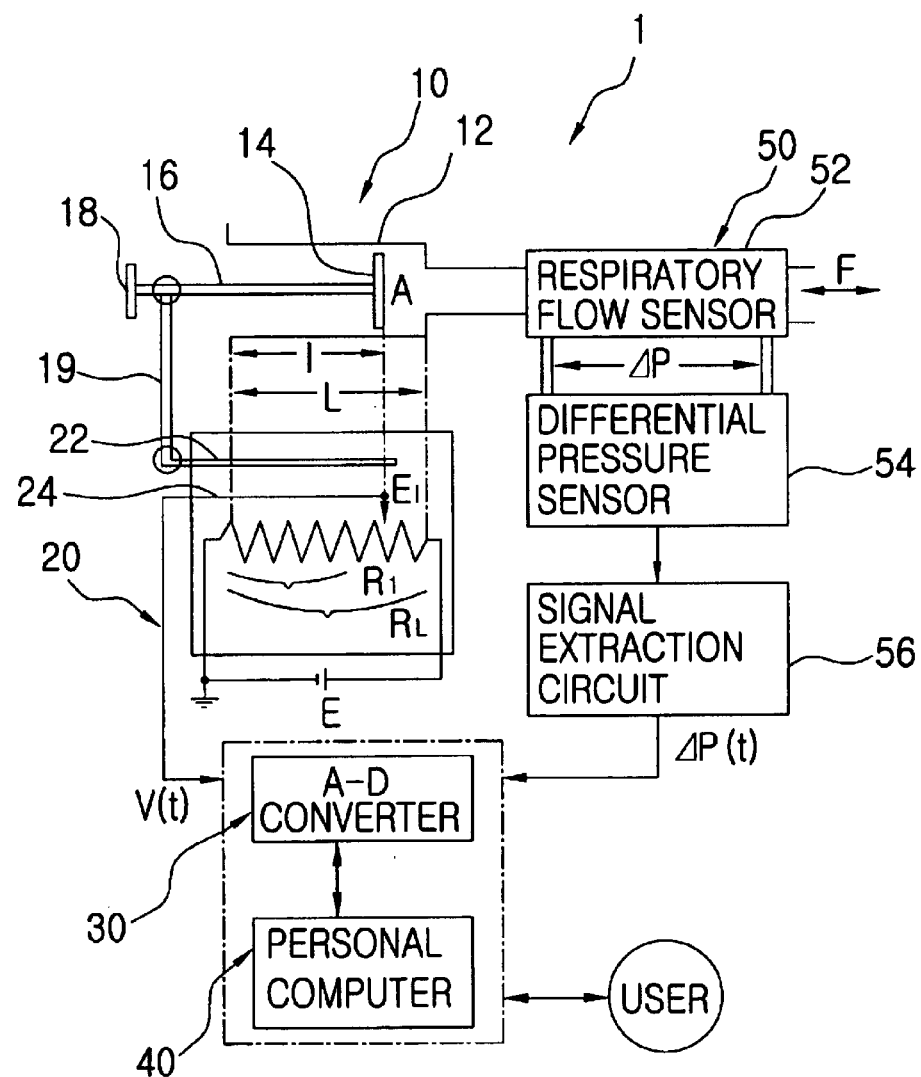
FIG. 1 is a view showing the construction of a system for obtaining respiratory flow measuring characteristic correction factors for a respiratory flow measuring device according to the present invention.

FIG. 1 is a view showing the construction of a system for obtaining respiratory flow measuring characteristic correction factors for a respiratory flow measuring device according to the present invention.

As shown in FIG. 1, the obtaining system 1 comprises a 3 L syringe 10, a detecting unit 20, an analog/digital (A/D) converter 30 and a computer 40. The 3 L syringe 10 is connected to a respiratory tube of a respiratory flow measuring device (hereinafter, referred to as pneumotachometer) 50 through a duct line. The detecting unit 20 detects volume variation within the syringe 10 and outputs the detected result as a voltage signal. The A/D converter 30 converts analog signals including a volume variation signal, detected as the voltage signal by the detecting unit 20, and a differential pressure variation signal, detected as a voltage signal by a differential pressure sensor 54 of the pneumotachometer 50 through a signal extracting circuit 56, into digital signals. The computer 40 computes the digital signals outputted from the A/D converter 30. In this case, the construction of the pneumotachometer is well known in the field, so the detailed descriptions thereof are omitted.

The 3 L syringe 10, which is a product recommended by the American Thoracic Society, consists of a cylinder 12, a piston 14 to reciprocate within the cylinder 12, and a piston load 16 to push the piston 14. In this case, a handle 18 is formed at the end of the piston load 16, and a lever member 19 is attached to a portion of the piston load 16 near the handle 18 to be extended perpendicularly to the syringe 10.

Further, the detecting unit 20 according to an embodiment of the present invention detects the position variation of the piston 14 within the syringe 10 (which is proportional to the volume variation within the sylinge) and outputs the detected result as a voltage signal.

The detecting unit 20 includes a sensing bar 22 attached perpendicularly to the lever member 19 or formed to be integrated with the lever member 19, and a linear resistor 24 constructed to come into contact with the sensing bar 22. The sensing bar 22 moves on the linear resistor 24 according to the reciprocation of the piston 14. At this time, a certain voltage E is applied to the resistor 24, so the detecting unit 20 outputs a voltage E1 proportional to the position variation of the piston 14 if the piston 14 reciprocates. In this case, a sectional area A of the piston 14 is constant, so the position variation of the piston 14 is proportional to the volume variation within the sylinge 12. Therefore, a volume variation signal according to the movement of the piston 14 is determined by the following Equation [5], $$V(t) = \frac{A \cdot L}{E} \cdot E_1(t) \quad [5]$$

where V(t) is collected in the personal computer 40 through the A/D converter 30, and an exact instantaneous flow value F(t) is obtained if V(t) is differentiated. These operations are performed by a program stored in the personal computer 40.

While the detecting unit 20 detects the volume variation signal, a differential pressure ΔP is generated in the respiratory flow sensor 52 of the pneumotachometer to be corrected. The differential pressure ΔP is outputted as a differential pressure variation signal, which is a voltage signal, through the signal extraction circuit 56 connected to the differential pressure sensor 54. In this case, both the differential pressure sensor 54 and the signal extraction circuit 56 are included in the pneumotachometer 50 and are well known in the field, so detailed descriptions thereof are omitted.

The volume variation signal and the differential pressure variation signal obtained through the above process are converted into RS-232C compatible signals through the A/D converter 30. The converted signals are computed by the computer 40 connected to the A/D converter 30. As the result of the computation, correction factors required to measure respiratory flow, that is, respiratory flow measuring characteristic coefficients and correction coefficients used to correct measurement values according to respiratory flow values are obtained.

Hereinafter, a method of obtaining respiratory flow measuring characteristic correction factors is described in detail using the obtaining system 1.

Figure 2:
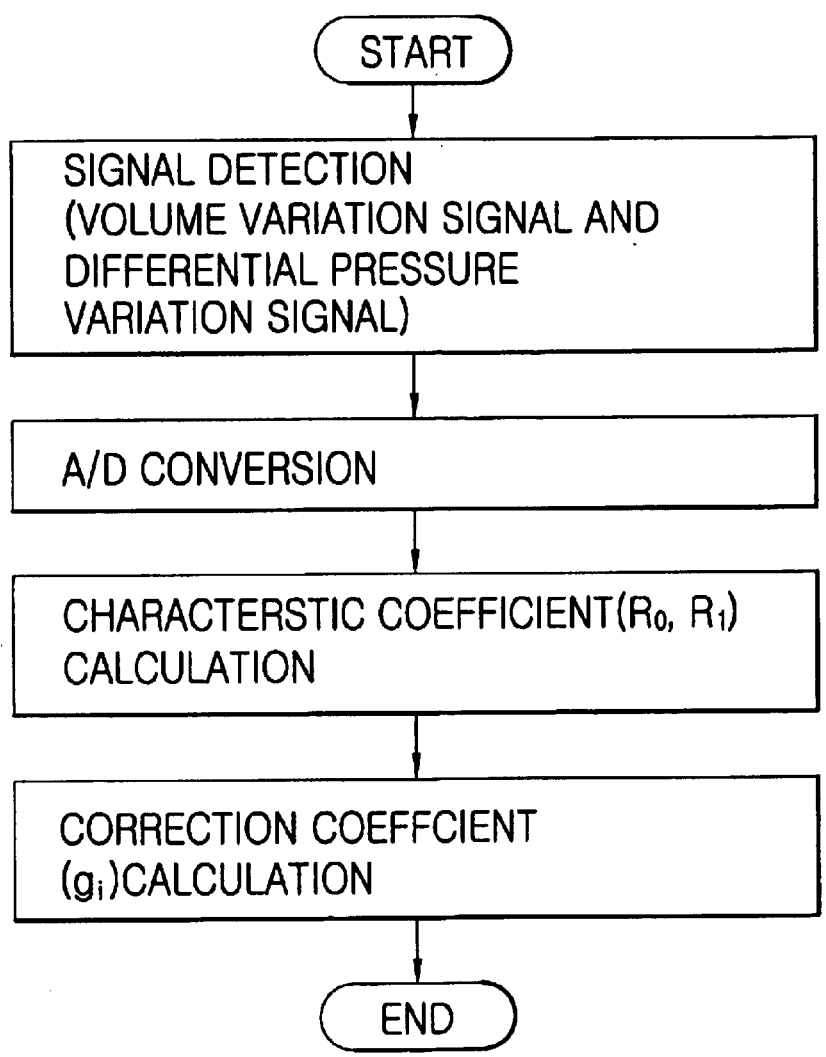
FIG. 2 is a flowchart of a method of obtaining respiratory flow measuring characteristic correction factors using the system of FIG. 1.

As shown in a flowchart of FIG. 2, the correction factor obtaining method comprises the steps of A/D converting the volume variation signal and the differential pressure variation signal into digital signals and calculating measuring characteristic coefficients $R_0$ and $R_1$ using the digital volume variation signal and differential pressure variation signal. The correction factor obtaining method may further comprise the step of calculating correction coefficients with respect to respective respiratory flow values using the coefficients $R_0$ and $R_1$, obtained at the above step.

The program stored in the computer 40 collects the volume variation signal V(t) and the differential pressure variation signal ΔP(t) which are converted into digital signals at the A/D convertion step, and calculates the characteristic coefficients $R_0$ and $R_1$ of Equations [1] and [2], which are respiratory flow measuring characteristic equations, by equations which will be described later. In order to obtain the characteristic coefficients, the instantaneous flow value F(t) obtained by differentiating the volume variation signal V(t) is used.

If Equation [1] is integrated according to respective strokes, based on the reciprocation of the piston 14 of the syringe 10, and arranged, the following Equation [6] can be obtained.

$$\frac{\int \Delta P(t)dt}{\int F(t)dt} = R_0 + R_1 \cdot \frac{\int F^2(t)dt}{\int F(t)dt} \quad [6]$$

In Equation [6], the integrated result of the instantaneous flow value F(t) is 3 L, so Equation [7] is obtained, $$\frac{\int \Delta P(t)dt}{3} = R_0 + R_1 \cdot \frac{\int F^2(t)dt}{3} \quad [7]$$

where F2(t) is obtained by squaring F(t) which is obtained by differentiating the volume variation signal. Further, if integral functions of both terms of Equation [7] are calculated according to strokes, the following Equation [8] is obtained, $y_k = R_0 + R_1 \cdot x_k$ $y_k = \int \Delta P_k(t)dt/3$ [8]

$x_k = \int F_k^2(t)dt/3$

In Equation [8], k is a stroke number such as 1, 2, ..., K.

As indicated in Equation [8], a set of linear equations are obtained, so linear regression analysis is carried out to calculate measuring characteristic coefficients $R_0$ and $R_1$ of Equations [1] and [2].

Since the measuring characteristic coefficients $R_0$ and $R_1$, calculated by the above process, are values which are obtained by simultaneously carrying out uniform correction of Equation [3] and reflecting the corrected results, an ultimate respiratory flow measuring characteristic equation is expressed by the following Equation [9], in which s of the Equation [4] is omitted.

$$F = \frac{\sqrt{R_0^2 + 4R_1 \cdot \Delta P} - R_0}{2R_1} \quad [9]$$

The measuring characteristic coefficients $R_0$ and $R_1$ of Equation [9] are values obtained by carrying out a syringe experiment (dynamic characteristic experiment). Therefore, if respiratory flow values measured by the pneumotachometer are corrected using the characteristic coefficients $R_0$ and $R_1$, measurement values that are more accurate than conventional respiratory flow measurement values based on a static characteristic experiment can be obtained.

On the other hand, a method of obtaining respiratory flow measuring characteristics correction factors according to another embodiment of the present invention further comprises the step of obtaining a correction coefficient used to correct volume measurement values according to flow values of airflow by using the characteristic coefficients $R_0$ and $R_1$ and the above-described differential pressure variation signal and volume variation signal as data.

This step, which employs a histogram summing method, considers the fact that most modern measuring devices are digitally operated.

Figure 3A:
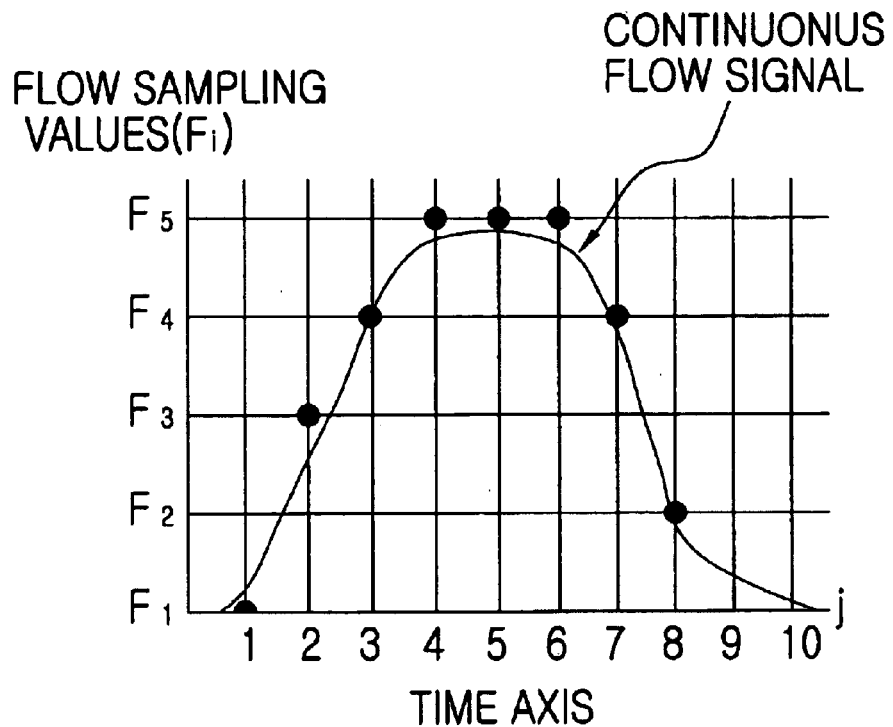
FIG. 3a is a graph showing a continuous flow signal according to time and discontinuous flow sampling values obtained by analog/digital (A/D) converting the flow signal in the system of the present invention.
Figure 3B:
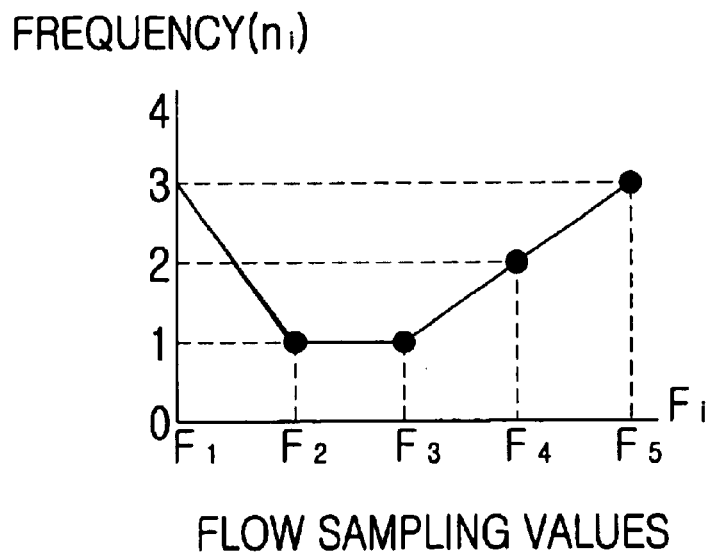

A/D conversion is a technique for enabling a computer to easily perform a computing operation by converting a continuous signal into discontinuous numerical information. As shown in FIG. 3*a*, if the continuous signal E(t) is A/D converted, F(t) is formed as a set of discontinuous values {F1, F2, ..., }. In this case, if the numbers of the same values of Fi of FIG. 3*a* are counted and a histogram is drawn up using the numbers, a distribution chart showing the frequency of each of specific values of F is obtained, as shown in FIG. 3*b*.

In fact, the A/D converted signal is the differential pressure variation signal, but the characteristic coefficients $R_0$ and $R_1$ are already known in Equation [9], so it is considered that the flow signal is directly A/D converted, and the remaining Equations are developed.

If digital flow values accumulated with respect to a specific k-th stroke among stroke data accumulated by the aforementioned manual reciprocation are integrated on a time axis, the following volume value is obtained. In this case, flow values are discontinuous, so an integral equation is changed to a summing equation, which is expressed by Equation [10].

$$\int_{k\text{-th stroke}} F(t)dt = T_s \cdot \sum_{j_k=1}^{N_k} F_i(j_k) \quad [10]$$

In Equation [10], Ts is a sampling interval for A/D conversion, $j_k$ is a j-th point on a time axis for a k-th stroke, $N_k$ is the total number of A/D converted flow values, and $F_i$ is an i-th discontinuous flow value (sample value). Equation [10] is formalized by applying the k-th stroke to j corresponding to the time axis of FIG. 3*a*.

At this time, if flow values of FIG. 3*a* are counted and a histogram is drawn up as shown in FIG. 3*b*, the frequency $n_{ik}$ of each of the flow sample values is obtained. Accordingly, if the frequency $n_{ik}$ is weighted to each of the sample values and the weighted results are summed up as indicated in Equation [11], the same value as the volume value of Equation [10] is obtained.

$$\sum_{j_k=1}^{N_k} F_i(j_k) = \sum_{i=1}^{M} n_{ik} \cdot F_i \quad [11]$$

In Equation [11], M is the total number of flow sample values obtained when A/D conversion is carried out. For example, referring to FIG. 3*a*, the sum in the left term of Equation [11] is the sum of A/D converted flow values, so the result thereof is F1+F3+F4+F5+F5+F5+F4+F2+F1+F1, and is arranged to be 3F1+F2+F3+2F4+3F5, which becomes equal to that of the right term of Equation [11]. That is, a volume value for a specific stroke is calculated, if frequencies $n_{ik}$ are counted according to flow sample values Fi obtained in the A/D conversion, instead of integration (or summation) on the time axis (j), a histogram is drawn up using the counted frequencies, and thereafter corresponding frequencies are weighted to the flow sample values, and weighted results are summed up. Therefore, if Equation [11] is applied to Equation [10], the following Equation [12] is obtained.

$$\int_{k\text{-th stroke}} F(t)dt = T_s \cdot \sum_{i=1}^{M} n_{ik} F_i \quad [12]$$

All the volume values Vc of Equation [12] would ideally be 3 L, but actual volume measurement values may vary according to errors of the coefficients $R_0$ and $R_1$, so a proportion coefficient $S_k$ is introduced according to strokes as indicated in the following Equation [13].

$$S_k \equiv \frac{V_C(=3)}{T_s \cdot \sum_{i=1}^{M} n_{ik} \cdot F_i} \quad [13]$$

Since flow values of Equation [13] are actually obtained from a pressure value, the flow values are newly derived from Equation [1] which is an experimentally-derived characteristic equation. Since $\Delta P = R(F) \cdot F$, the following Equation [14] is obtained if $G(F)=1/R(F)$, which is a reciprocal number of $R(F)$, is introduced.

$$F = G(F) \cdot \Delta P, \text{ where } G(F) = \frac{1}{R_0 + R_1 \cdot F} \quad [14]$$

In Equation [14], since $G(F)$ representing measuring characteristics may not be ideal, the following Equation [15] is obtained if a coefficient $g(F)$ for correcting $G(F)$ according to flow values is introduced.

$$F = g(F) \cdot G(F) \cdot \Delta P \quad [15]$$

In Equation [15], g will be ideally "1" regardless of the values of F. Further, if values of g can be appropriately determined to be values adjacent to "1" according to errors of the experimentally-derived equation, random errors are corrected according to flow values by the values of g, thus obtaining an exact value of F. If Equation [9] is applied to a relation of F–$\Delta$P obtained from Equations [14] and [15] and arranged, the following Equation [16] is obtained.

$$F = g\{f(\Delta P)\} \cdot G\{f(\Delta P)\} \cdot \Delta P, \quad [16]$$
$$\text{where } f(\Delta P) = \frac{\sqrt{R_0^2 + 4R_1 \cdot \Delta P} - R_0}{2R_1}$$

In Equation [16], since A/D conversion is carried out while the correction coefficient g is not known, the flow sample value $F(i)$ can be obtained if g is assumed to be "1" and Equation [16] is used. Accordingly, by using the sample values $\Delta P_i$ of the differential pressure variation signal which is actually A/D converted, the Equation [13] can be modified to Equation [17] from Equations [9], [14] and [16].

$$S_k = \frac{V_C}{T_s \sum_{i=1}^{M} n_{ik} \cdot G_i \cdot \Delta P_i} \quad [17]$$

$$\text{where } G_i = G\{f(\Delta P_i)\} = \frac{1}{R_0 + R_1 \cdot f(\Delta P_i)}$$

$$f(\Delta P_i) = \frac{\sqrt{R_0^2 + 4R_1 \cdot \Delta P_i} - R_0}{2R_1}$$

In Equation [17], $S_k$ is the ratio of the actual volume value $V_C$ of the syringe to a volume measurement value (denominator of the right term of Equation [17] which includes measurement error and is measured by the flow sensor. Further, $S_k$ is determined from differential pressure information accumulated with respect to all strokes (k=1, 2, ..., K) accumulated during the manual reciprocation of the piston.

After the coefficients $R_0$ and $R_1$ are calculated using stroke data accumulated during the manual reciprocation, a histogram is drawn up for strokes using the same data as the accumulated stroke data, and the proportional coefficient $S_k$ is then calculated by Equation [17].

As described above, the correction coefficient, such as g of Equation [16], are introduced according to flow values of the flow measuring characteristic equation. If values of the correction coefficient g are precisely determined, the integrated value of Equation [16] must be equal to the volume value $V_C$ of the syringe, so the following Equation [18] is obtained.

$$V_C = \int_{k-th \; stroke} F(t) dt \quad [18]$$
$$= \int_{k-th \; stroke} g\{f(\Delta P)\} \cdot G\{f(\Delta P)\} \cdot \Delta P(t) dt$$

If Equation [18] is modified to be an A/D converted form by using a histogram summing method, the following Equation [19] is obtained.

$$V_C = T_s \cdot \sum_{i=1}^{M} g_i \cdot n_{ik} \cdot G_i \cdot \Delta P_i \quad [19]$$

If Equation [19] is applied to Equation [17] and arranged, Equation [20] is obtained.

$$\sum_{i=1}^{M} g_i \cdot n_{ik} \cdot G_i \cdot \Delta P_i = S_k \cdot \sum_{i=1}^{M} n_{ik} \cdot G_i \cdot \Delta P_i \quad [20]$$

The above Equation [20] is an equation corresponding to a specific stroke, so Equation [20] must be established with respect to all strokes (k=1, 2, ..., K), and must be satisfied even if the left and right terms are summed for the values of k, respectively. Therefore, the following Equation [21] is obtained.

$$\sum_{k=1}^{K} \sum_{i=1}^{M} g_i \cdot n_{ik} \cdot G_i \cdot \Delta P_i = \sum_{k=1}^{K} S_k \cdot \sum_{i=1}^{M} n_{ik} \cdot G_i \cdot \Delta P_i \quad [21]$$

In the right term of Equation [21], it doesn't matter that $S_k$ is inserted into a second sigma and summing orders of k and i are exchanged, so the following Equation [22] is obtained.

$$\sum_{k=1}^{K} \left( \sum_{i=1}^{M} g_i \cdot n_{ik} \right) \cdot G_i \cdot \Delta P_i = \sum_{k=1}^{K} \left( \sum_{i=1}^{M} S_k \cdot n_{ik} \right) \cdot G_i \cdot \Delta P_i \quad [22]$$

In Equation [22], if values in parentheses of both terms are the same, equality is satisfied. Further, since the correction coefficient gi is not related to k, it can be obtained by Equation [23] if gi is taken out of the k sigma and Equation [22] is arranged.

$$g_i = \frac{\sum_{k=1}^{K} n_{ik}}{\sum_{k=1}^{K} S_k \cdot n_{ik}} \quad [23]$$

That is, a volume measurement value is calculated by drawing up the histogram according to strokes using differential pressure information accumulated in the manual reciprocation experiment of the piston of the syringe, the ratio $S_k$ of the actual volume value to the volume measurement value is obtained, and further the ratio $S_k$ is applied to Equation [23], thus the correction coefficient gi may be easily obtained.

Now, since the correction coefficient g has been determined, respiratory flow is only measured using Equation [18] for new airflow.

If g is once determined, g·G (with reference to Equation [18]) becomes a new value of G, so the repeated performance of Equation [18] is only needed if recorrection is required. At this time, a volume signal for a correction factor obtaining system is required.

Figure 7:
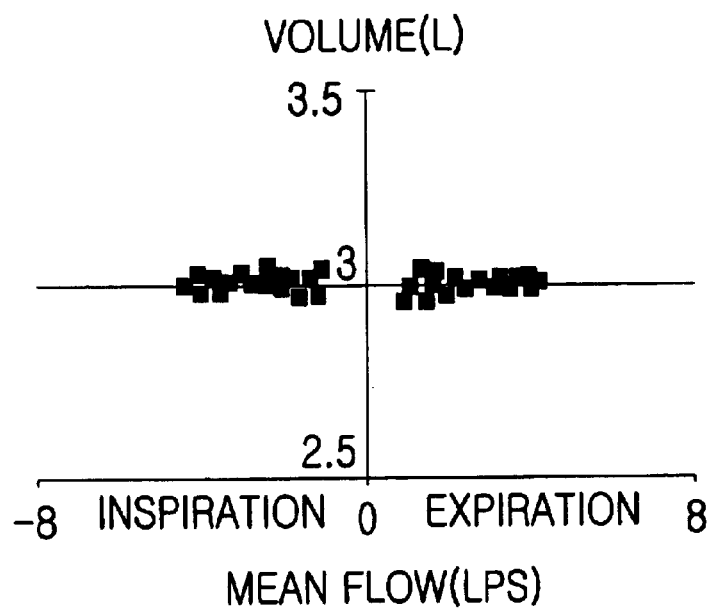
FIG. 7 is a graph showing the example of measurement of volume versus mean flow when respiratory flow is measured using the correction coefficient obtained by the present invention.
Figure 9:
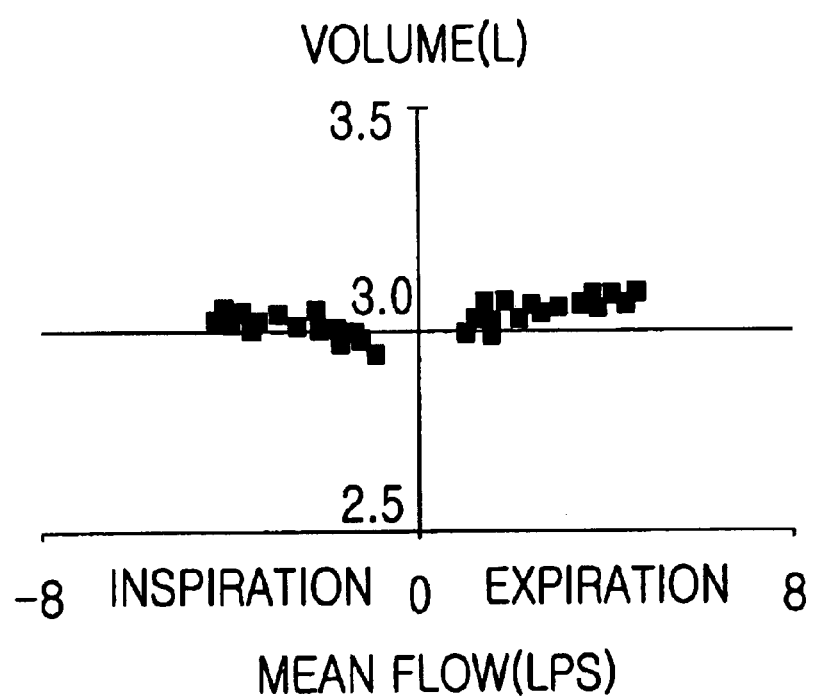
FIG. 9 is a graph showing the volume and mean flow obtained by applying the same coefficients obtained by a conventional static characteristic experiment to a syringe experiment.

FIG. 7 shows the example of volume and mean flow measured using the correction factors (characteristic coefficients and correction coefficients) obtained by the above correction factor obtaining method. This measurement example shows that errors are greatly reduced compared to the example of FIG. 9 showing volume and mean flow measured using correction factors obtained by the conventional method.

Figure 8:
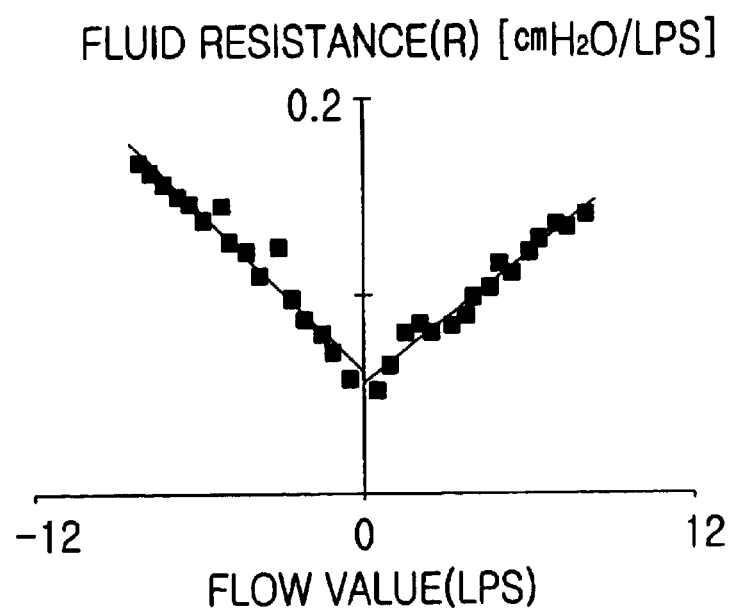
FIG. 8 is a graph showing the result of measurement of conventional static characteristics of a pneumotachometer, wherein fluid resistances according to flow values are depicted.

In order to prove the usefulness of the method of obtaining characteristic coefficients and the correction coefficient of the present invention, a 3 L syringe experiment for volume correction was carried out for 250 strokes. Fluid resistor characteristics (FIG. 8) obtained from the static characteristic experiment were equally applied to the differential pressure variation signal with respect to all of 250 strokes to calculate a flow signal according to strokes by Equation [2]. Further, if the flow signal is integrated to calculate a volume value (protocol RF), the mean value of relative errors between the calculated volume value and an actual volume value of the syringe was 4.7%.

After 250 strokes were grouped into five sets of 50 strokes, characteristic coefficients $R_0$ and $R_1$ were calculated using the 50 stroke data of a first set by the above proposed Equations [7] and [8], and volume values were calculated according to Equation [9] (protocol LC). As a result, the mean value of relative errors was reduced to 2.3%.

Further, after the correction coefficient gi of Equation [23] was determined by using the characteristic coefficients $R_0$ and $R_1$ obtained from the first of five sets of data and applying a histogram summing method, volume values were calculated by Equation [16] (protocol RS). As a result, the mean value of relative errors was reduced to 0.8%, which represents the measurement of high precision, only ⅓ of the 3% limit, which is a limit recommended by the American Thoracic Society.

Figure 4:
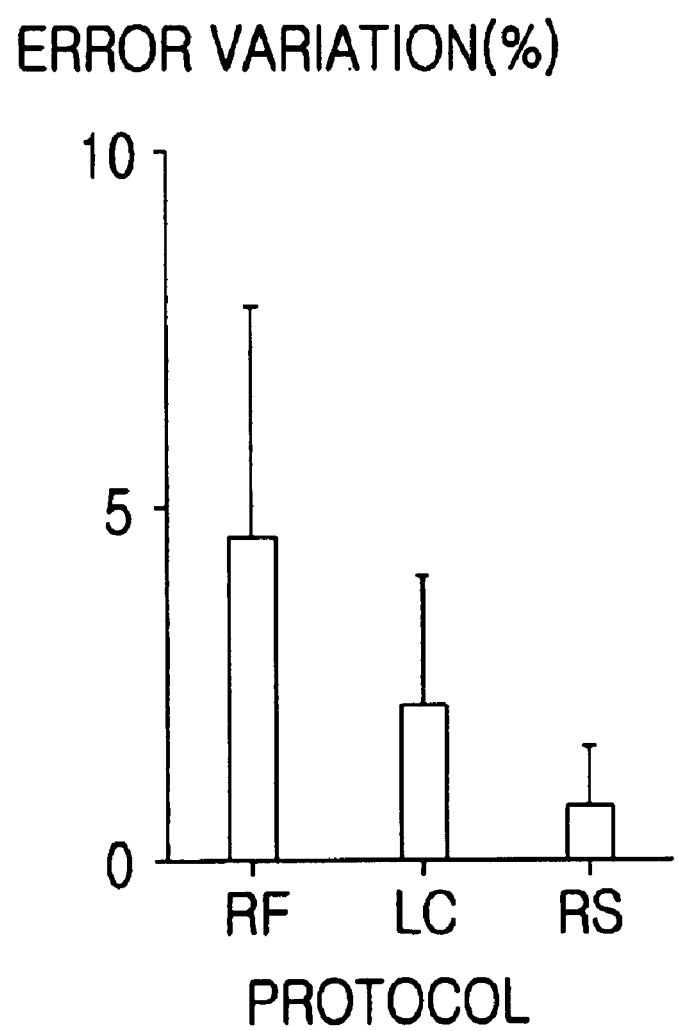
FIG. 4 is a graph showing volume errors based on the application of a conventional correction method (RF) and correction methods (LC and RS) of the present invention.

That is, as the result of determination of the characteristic coefficients $R_0$ and $R_1$ and application of the histogram summing method according to the present invention, errors are greatly reduced, and ultimately measurement of high precision having an error range within 1% is possible. Error reduction effects based on the application of correction methods according to steps are depicted in FIG. 4.

Figure 5:
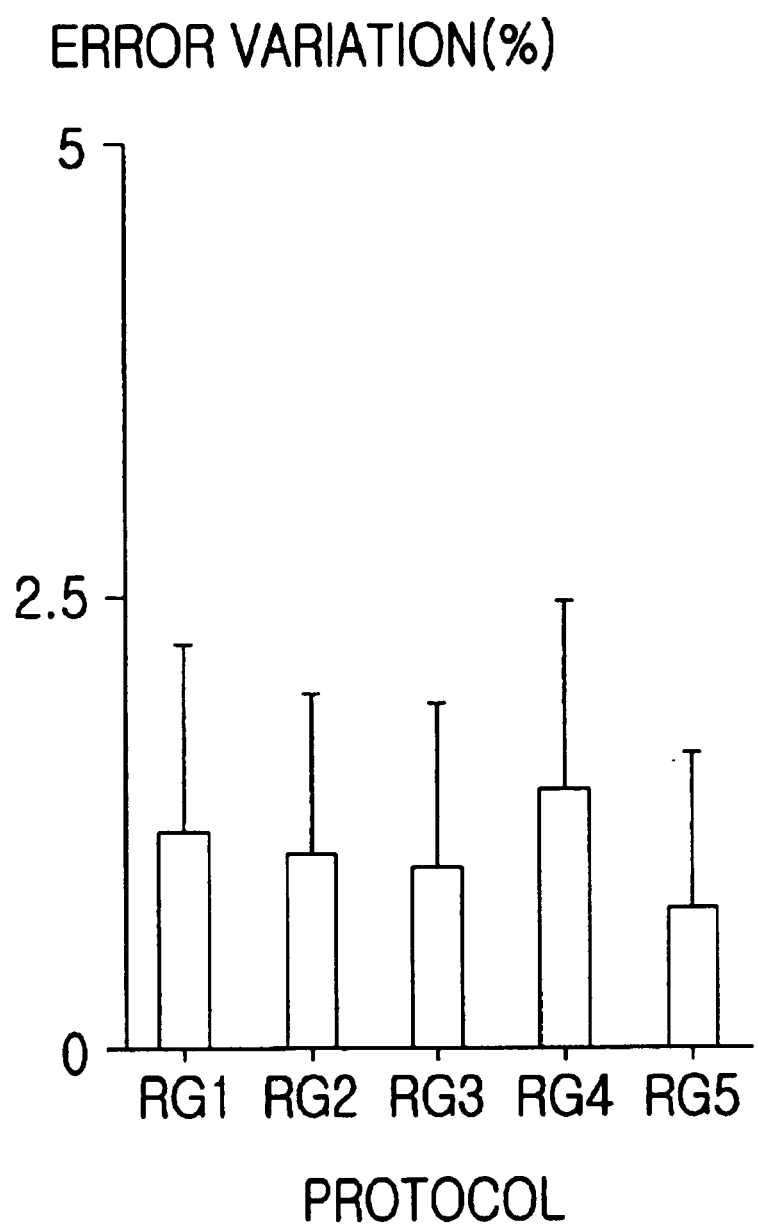
FIG. 5 is a graph showing an error variation (mean±standard deviation) when correction coefficients obtained by the present invention are applied to new data.

If volume values are calculated by applying the same correction coefficient obtained from the fifth set to the first and fourth sets (protocol RG1 to 4), the mean value of relative errors was slightly increased to 1.2% with reference to FIG. 5, but it can be seen that relative errors are maintained to be lower than 1.5%. These relative errors indicate that the correction method of the present invention is consistently carried out.

Figure 6:
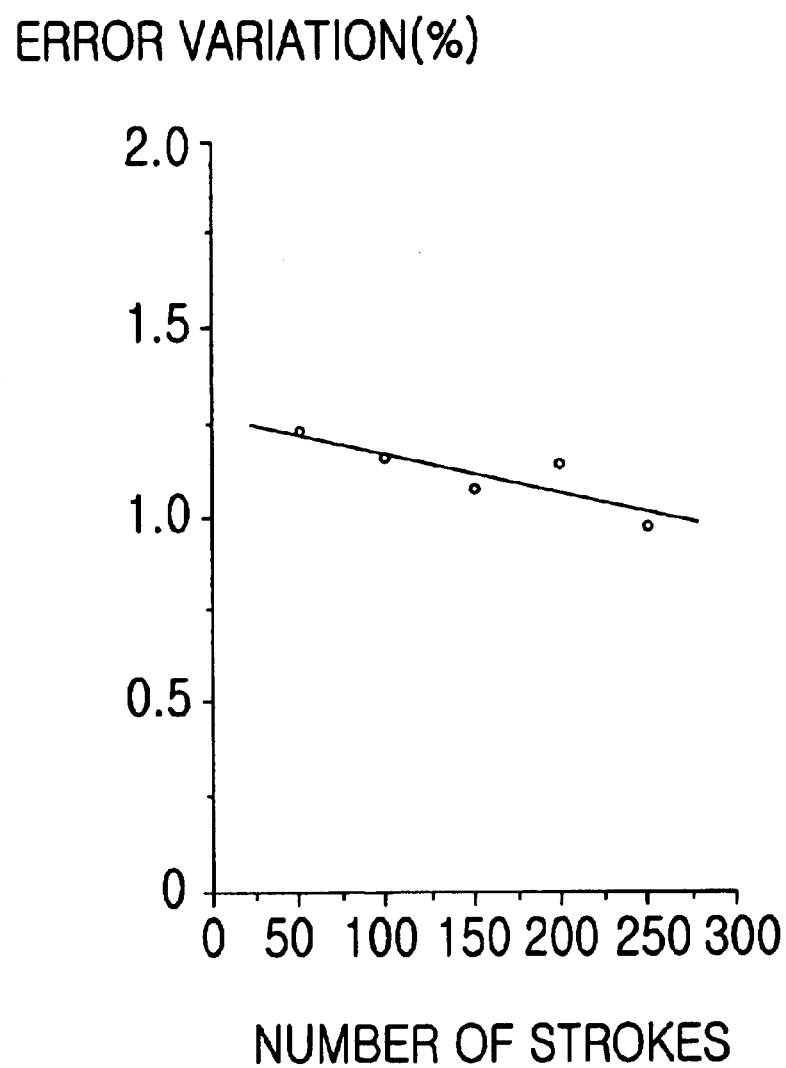
FIG. 6 is a graph showing an error variation according to the amount of data used for obtaining the correction coefficient.

Further, if volume measurement errors are calculated while the number of strokes used to calculate the correction coefficient is increased from 50 to 250, the measurement errors were gradually reduced as shown in FIG. 6. However, the reduction rate of the measurement errors (0.05%/50 strokes) was slight. Therefore, FIG. 6 proves that sufficiently precise measurement can be performed even if reciprocations of only 20 to 30 strokes are carried out, which indicates that the method of the present invention can be practically utilized under clinical environments.

As described above, the present invention provides a system and method of obtaining characteristic measurement correction factors for a respiratory flow measuring device, which does not separately carry out a process of determining characteristic coefficients used in characteristic equations for respiratory flow measurement (static characteristic experiment), and a volume correcting process (syringe experiment), thus reducing time and effort required to carry out the processes. Further, the present invention is advantageous in that, since it does not carry out a static characteristic experiment, errors due to the division of calibration into two processes can be removed, thus improving the precision of actual measurement. Further, the present invention is advantageous in that it employs only a distance sensor without an additional airflow generating device, and performs signal analysis using a typical A/D converter and a personal computer, thus economically obtaining measurement correction factors.

Moreover, the present invention is advantageous in that, since it can correct errors of volume measurement values by calculating correction coefficients according to each flow values by a histogram summing method, random errors inevitably included in experimental characteristic equations can be consistently corrected.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A system for obtaining measuring characteristic correction factors for a respiratory flow measuring device using a static pressure difference, comprising:

a syringe connected to a respiratory tube of the respiratory flow measuring device through a duct line;

a detecting unit for detecting volume variation within the syringe and outputting the detected result as a voltage signal;

an analog/digital (A/D) converter for converting analog signals including a volume variation signal detected as the voltage signal by the detecting unit and a differential pressure variation signal detected as a voltage signal by a differential pressure sensor connected to the respiratory flow sensor of the respiratory flow measuring device through a signal extraction circuit into digital signals; and a computer for obtaining measuring characteristic correction factors using the digital signals outputted from the A/D converter wherein said detecting unit comprises:

a sensing bar connected to an end portion of a piston handle of the syringe for reciprocating in parallel with a piston of the syringe; and a linear resistor for converting position variation of the piston into a voltage signal by coming into contact with the sensing bar, wherein a voltage is applied to the linear resistor.

2. A method of obtaining measuring characteristic correction factors required for respiratory flow measurement using a measuring characteristic correction factor obtaining system, the system having a syringe connected to a respiratory tube of a respiratory flow measuring device through a duct line, a detecting unit for detecting volume variation within the syringe and outputting the detected result as a voltage signal, an analog/digital (A/D) converter connected to the detecting unit and a computer for collecting information converted by the A/D converter to obtain measuring characteristic correction factors for a respiratory flow measuring device, comprising the steps of:

converting analog signals including a volume variation signal outputted from the detecting unit and a differential pressure variation signal detected by a differential pressure sensor of the respiratory flow measuring device as a voltage signal into digital signals; and calculating characteristic coefficients $R_0$ and $R_1$ of a first equation by applying an instantaneous flow value $F(t)$ obtained by differentiating the converted volume variation signal $V(t)$ and the converted differential pressure variation signal $\Delta P(t)$ to a second equation, $$\begin{aligned}\Delta P &= R(F) \cdot F \quad \text{[first equation]}\\ &= (R_0 + R_1 F) \cdot F \\ &= R_0 F + R_1 F^2\end{aligned}$$

$y_k = R_0 = R_1 \cdot x_k$, where $y_k = \int \Delta P_k(t)dt/3$, and $x_k = \int F_k^2(t)dt/3$, and k is a stroke number.

3. The measuring characteristic correction factor obtaining method according to claim 2, further comprising the steps of drawing up a histogram according to strokes using differential pressure variation signal information accumulated in a manual reciprocation experiment of the syringe to calculate a volume measurement value after, calculating the measuring characteristic coefficients $R_0$ and $R_1$, obtaining the ratio $S_k$ of an actual volume value to the volume measurement value, and calculating a correction coefficient gi for correcting the volume measurement value according to respiratory flow values by applying the ratio $S_k$ to the following equation $$g_i = \frac{\sum_{k=1}^{K} n_{ik}}{\sum_{k=1}^{K} S_k \cdot n_{ik}}.$$

* * * * *